United States Patent [19]
Brisson et al.

[11] Patent Number: 5,240,002
[45] Date of Patent: Aug. 31, 1993

[54] ULTRASOUND TRANSDUCER SHIELDING

[75] Inventors: A. Glen Brisson, Kildeer; Exequiel Dela Cruz, Arlington Heights; Dianne L. Vickers, Cary, all of Ill.

[73] Assignee: Bantum Tripter Joint Venture Partners, Columbus, Ohio

[21] Appl. No.: 856,373

[22] Filed: Mar. 23, 1992

[51] Int. Cl.$^5$ .................... A61B 17/22; A61B 8/00
[52] U.S. Cl. ................... 128/660.03; 128/24 EL
[58] Field of Search ............. 128/24 EL, 660.03; 367/147

[56] References Cited

U.S. PATENT DOCUMENTS

| | | | |
|---|---|---|---|
| 4,844,081 | 7/1989 | Northeved et al. | 128/660.03 |
| 4,915,114 | 4/1990 | Hassler | 128/24 EL |
| 4,928,672 | 5/1990 | Grasser et al. | 128/24 EL |
| 4,947,830 | 8/1990 | Rattner et al. | 128/24 EL |
| 5,009,232 | 4/1991 | Hassler et al. | 128/660.03 |
| 5,025,789 | 6/1991 | Hassler | 128/660.03 |
| 5,031,626 | 7/1991 | Hassler et al. | 128/660.03 |
| 5,058,569 | 10/1991 | Hassler et al. | 128/24 EL |

FOREIGN PATENT DOCUMENTS

| | | | |
|---|---|---|---|
| 0441997 | 8/1991 | European Pat. Off. | 128/24 EL |
| 3942253 | 6/1991 | Fed. Rep. of Germany | 128/660.03 |

Primary Examiner—Lee S. Cohen
Assistant Examiner—Krista M. Pfaffle
Attorney, Agent, or Firm—Robert M. Wolters

[57] ABSTRACT

An extracorporeal lithotripter is provided with an ultrasound transducer on the rotational center line of the reflector and substantially at the open end of the reflector. The transducer is protected against shockwaves by a metallic housing in which it is mounted. The transducer at one end engages the housing through a resilient plastic disk, and is spaced laterally from the housing by a rubber O-ring adjacent the open end of the housing. The housing directly shields or shadows the transducer so that shockwaves are not transmitted to the transducer, which could damage the transducer and shorten its life.

11 Claims, 1 Drawing Sheet

ULTRASOUND TRANSDUCER SHIELDING

BACKGROUND OF THE INVENTION

Extracorporeal lithotripters for the noninvasive disintegration of kidney stones are well known. Such lithotripters use a truncated ellipsoidal reflector with an open end that is closed by a rubber or the like diaphragm. The interior of the reflector and the space defined by the diaphragm are filled with water. A spark gap is provided at the first focus point of the reflector. The second focus point of the reflector is positioned outside of the reflector and beyond the diaphragm. The reflector and the patient are moved relative to one another to position the second focus point on the kidney stone or other bodily concretion to be disintegrated. A spark across the spark gap flashes some of the water into steam and generally produces a shockwave. The shockwave is focused by the reflector and passes through the water in the reflector, through the diaphragm, and through bodily tissues to the kidney stone on which it is focused. A succession of such shockwaves reduces the kidney stone to small fragments that readily pass out of the body with the urine.

In many sophisticated lithotripters the positioning is done by means of X-rays or ultrasound. As is known, the amount of exposure permitted to X-rays is limited. Ultrasound devices are usually interconnected with a computer so that when the kidney stone is properly located by the ultrasound transducer the computer relatively moves the patient and the reflector to cause the second focus point to coincide with the kidney stone. Such use of a computer and centering mechanisms materially increases the cost of the lithotripter, and thereby makes it unavailable to many prospective patients.

Use of an ultrasound transducer mounted within the lithotripter reflector and on the rotational axis thereof is disclosed in U.S. Pat. No. 4,620,545 issued to Shene, Nowacki and Brisson. A conical shield is interposed between the spark gap and the ultrasound transducer. However, no details are disclosed as to the mounting of the shield or the transducer relative to the reflector, or relative to one another.

OBJECTS AND SUMMARY OF THE PRESENT INVENTION

It is an object of the present invention to provide a housing or shield in a lithotripter reflector which is supported directly from the reflector, and which in turn supports the transducer in such manner as to shadow the transducer, and otherwise shield the transducer against shockwaves.

In carrying this out, a brass housing is provided, having a domed end disposed toward the spark gap. The housing deflects or reflects shockwaves. Furthermore, the brass construction is such as to prevent transmission of shockwaves with any efficiency. The transducer is mounted within the housing, both being centered on the axis of rotation of the reflector, and is spaced along its sides from the housing by an air jacket so that no shockwave can be transmitted to the sides. The end of the transducer closest to the spark gap is positioned relative to the shield or housing by a DELRIN plastic housing which does not efficiently transmit vibrations from the housing to the transducer. The transducer otherwise is connected to the housing only by an O-ring at the end of the housing, and which is an extremely inefficient transmitter of shocks or vibrations.

THE DRAWING

FIG. 1 is an axial sectional view through a lithotripter reflector and ultrasound transducer constructed in accordance with the present invention.

DETAILED DESCRIPTION OF THE ILLUSTRATED EMBODIMENT

Figure 1:
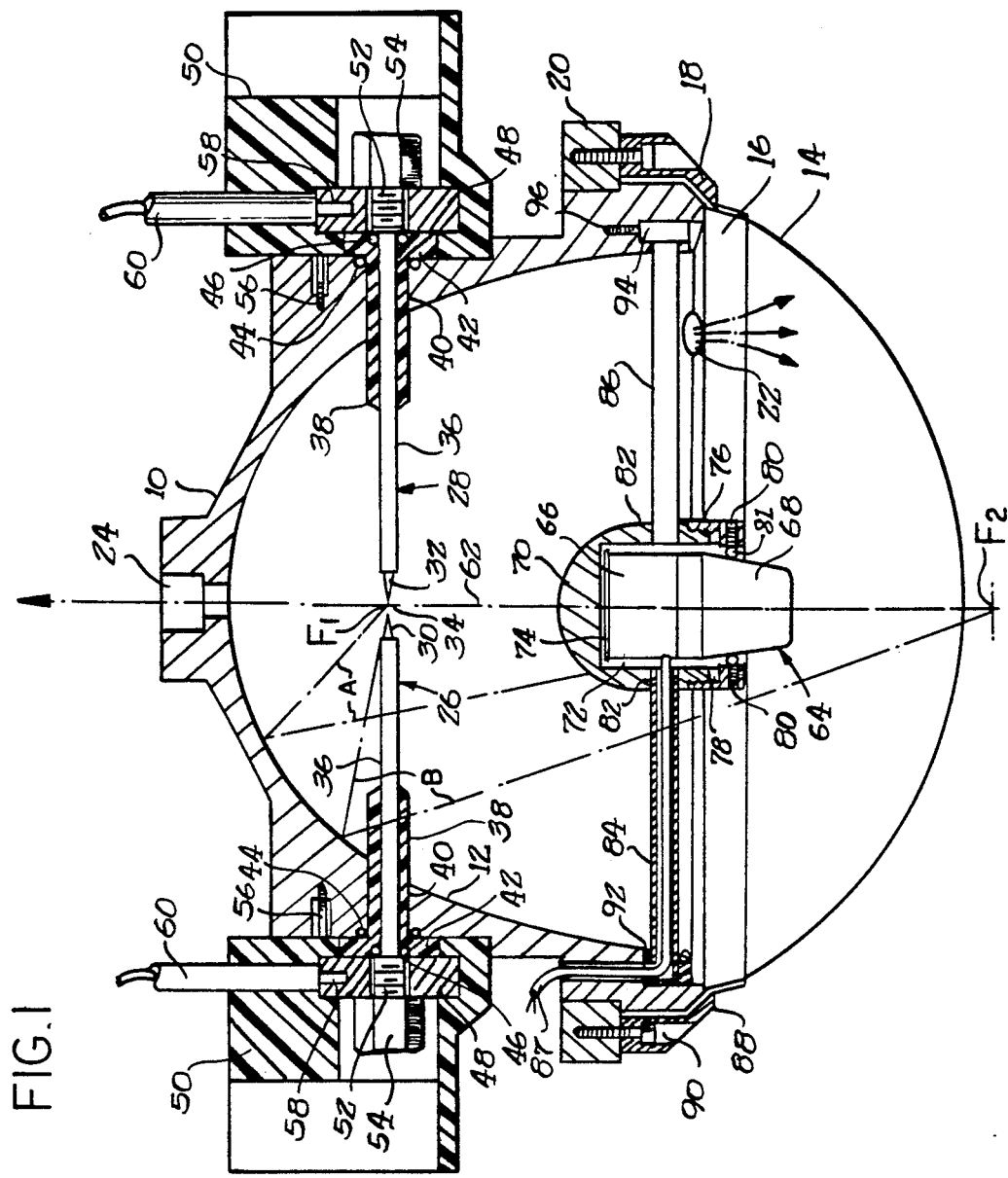

Referring first to FIG. 1, a lithotripter reflector assembly 10 has an ellipsoidal reflector surface 12. The reflector is aimed downwardly, and has an open lower end closed by a rubber diaphragm 14 gripped against a ring 16 at the open end of the reflector by gripping structure 18 secured to a ring 20 encircling the reflector and forming a part of the assembly. The reflector has a first focus point $F_1$ within the reflector and relatively toward the top thereof. There is a second focus point $F_2$ which is disposed beyond the diaphragm 14 and is intended for superposition on a kidney stone or the like within the body of a patient. An opening 22 in the ring 16 provides for entrance of water, and an opening 24 at the apex of the reflector provides for the exit of water. The plumbing connections are not pertinent to the present invention and are not further shown.

A pair of electrodes 26 and 28 extend into the reflector in alignment with one another. The electrodes have spaced, tapered metallic tips 30 and 32, respectively, providing between them a gap 34 coincident with the first focus point F1. A high voltage spark across the gap causes some of the water in the reflector to be flashed into steam and sets up a shock wave that is reflected by the walls of the reflecting surface or reflector 12. The electrodes 26 and 28 are mainly made of brass, and each is covered by an insulating silicone rubber sleeve 36. Each sleeve in turn is held within a plastic bushing 38 received in a respective bore 40 in the reflector assembly. Each bushing 38 has a head or flange 42 which extends radially outwardly from the axis of the respective bushing 38. An O-ring 44 is disposed beneath each flange or head 42 within a circular recess in the outer surface of the reflector housing. There is also an O-ring 46 recessed into each head and encircling the respective electrode.

A brass nut member or connector 48 is cast within each of a pair of plastic mounting members 50 made of an epoxy casting material. Each such nut member has a threaded bore through which a thicker, threaded portion 52 of the respective electrode is threaded. A hexagonal head member 54 on each electrode outer end is grippable by a wrench for threading an electrode into or out of position. Each mounting cast plastic member 50 is secured at 56 to the reflector housing. The stripped ends 58 of a pair of connecting wires 60 are secured within the brass nut members 48, and lead to spark generating apparatus, as is known in the art.

The reflector surface 12 has an axis of rotation 62, and both focus points $F_1$ and $F_2$ are on this axis. Also disposed on this axis and aimed toward the second focus point $F_2$ is an ultrasound transducer 64. The actual transducer is disposed within a plastic housing 66 which is cylindrical in its upper part. The housing further has a frustoconical tapered nose 68. As will be apparent, the housing is cylindrical about the axis of rotation 62.

The transducer 64 is mounted within a heavy brass housing 70 having a domed upper part, and cylindrical sides. A cylindrical bore 72 extends up into the housing from the lower end thereof, and the ultrasound housing at the upper end butts against a DELRIN plastic spacer disk 74. The side walls of the cylindrical portion 66 and the upper part of the tapered nose 68 are spaced from the walls of the bore 72. A retaining ring 76 is threaded on the lower end of the brass housing 70, and through a positioning ring 78 carrying a resilient O-ring 81 is adjusted by means of three equally arcuately spaced set screws 80 for final precision alignment of the transducer housing to aim the transducer specifically at the focus point $F_2$.

The brass housing 70 is provided with aligned opposite lateral or radial bores 82, and mounting arms 84 and 86 extend diametrically therefrom. It will be noted that the arms 84 and 86 are shown in FIG. 1 as lying in the same plane as electrodes 36. Actually, the arms are at right angles to the electrodes, and are shown in the common plane for ease of illustration. The left arm 84 is hollow and carries electric wiring 87 extending to the ultrasound transducer. The right arm 86 may be either hollow or solid. Both arms are made of stainless steel, and are brazed to the brass housing 70.

A stainless steel block 88 is brazed to the outer end of each of the arms 84 and 86. The left block 88 is provided with a passageway 90 to accommodate the wire 87 leading to the transducer. An O-ring 92 encircles the arm 84 adjacent the block 88 to prevent water from leaking from the reflector to the wiring. Each block 88 is machined and ground to precise specifications for precise location of the transducer 64. Each block 88 is provided with a pair of vertical bores 94 through which extend a pair of screws 96 to secure the block in position. The two blocks, the two arms, and the transducer housing are all brazed to one another in a fixture which assures proper relative positioning of the parts.

Each block 88 is received in a recess 98 which extends radially into the reflector assembly 10 and extends vertically upwardly therein at 100. The recesses 98 are very carefully milled, and may be ground as necessary, to ensure precise dimensioning so that the blocks will accurately position the reflector 70, through the respective arms 84 and 86. Thus, only slight correction of the positioning of the transducer 64 is necessary by way of the screws 80. The opposite ends of each block 88 and the corresponding mating portions of the recesses 98 are semicylindrical in nature. Further details of the blocks and recesses may be found in co-pending application Ser. No. 07/856,374, filed Mar. 23, 1992 by the same inventors.

As will be apparent, the portion of the shockwave generated at the first focus point $F_1$ will directly engage the housing 70, and will also engage it indirectly by reflection from the ellipsoidal surface 12. The brass housing is relatively massive, and generally will protect the transducer 64 from the shockwaves. As will be seen, the nose 68 of the transducer extends beyond the housing, but is adequately shadowed by the housing so that reflected shockwaves will not engage in any significant amount. Thus, the transducer is well shielded from the shockwaves. However, with the shockwave environment around the transducer, the transducer may eventually be damaged, but is very quickly replaced by removal of the two pairs of mounting screws to remove the blocks from the recesses in which they are received. Another transducer assembly then is installed by reversal of the process.

A first shockwave path is shown at A. This shockwave reflected path engages the transducer housing 70 near the upper portion thereof, and is deflected therefrom, and is substantially of no use. A second shockwave path B is shown in dot-dash lines. This one clears the lower portion of the housing, but the housing shadows the lower portion of the ultrasound transducer, so that this shockwave path is not allowed to engage the transducer. It will be apparent that other paths can be established, and that there is no possible way for a wave either directly or reflected from the surface of the reflector to engage the transducer. In addition, the air space 72 around the transducer prevents any possible shocks or vibrations to be transmitted from the side of the housing to the ultrasound transducer. The DELRIN plastic disk 74 at the top of the ultrasound transducer is a poor transmitter of energy, whereby substantially no vibration or shock can get through to the upper end of the ultrasound transducer. The ultrasound transducer is otherwise connected to the housing only through the O-ring 80 engaging the tapered nose, and this O-ring is made of rubber, and hence is a very poor transmitter of vibrational or shock energy. Consequently, it will be seen that the housing substantially protects the ultrasound transducer from the shockwaves found in the reflector.

The specific example of the invention as herein shown and described is for illustrative purposes only. Various changes in structure will no doubt occur to those skilled in the art, and will be understood as forming a part of the present invention in so far as they fall within the spirit and scope of the appended claims.

The invention is claimed as follows:

1. In an extracorporeal lithotripter comprising a truncated ellipsoidal reflector open at one end, a rubber diaphragm closing said open end, said reflector having a first focus point within said reflector and a second focus point outside said reflector and beyond said diaphragm, said reflector having an axis of rotation which passes through both of said focus points, said reflector and said diaphragm comprising a volume filled with water, a pair of electrodes in said reflector and having ends in spaced relation providing a spark gap at said first focus point, an electrical spark between said electrodes across said gap producing shockwaves focused by said reflector on said second focus point, the improvement comprising an ultrasound transducer within said reflector and aimed toward said second focus point, and a dense housing for said transducer, said housing being supported from said reflector adjacent said reflector open end and having a tapered end disposed toward said spark gap to deflect said shockwaves, said housing having an open end and a bore opening at said housing open end and aimed toward said second focus point, said bore having an inner end, said transducer being mounted in said bore and laterally spaced therefrom, resilient means interposed between said transducer and said bore inner end for cushioning said transducer, and additional resilient means substantially at said housing open end for spacing said transducer laterally from said housing for retaining and positioning said transducer.

2. The combination as set forth in claim 1 wherein said transducer has a substantially cylindrical portion within said bore and a tapered nose projecting from said housing and engaged by said additional resilient means.

3. The combination as set forth in claim 1 wherein the additional resilient means comprises an O-ring.

4. The combination as set forth in claim 2 wherein the additional resilient means comprises an O-ring.

5. The combination as set forth in claim 1 wherein the transducer is laterally spaced from said bore by an air gap between said additional resilient means and said bore inner end.

6. The combination as set forth in claim 5 wherein said transducer has a substantially cylindrical portion within said bore and a tapered nose projecting from said housing and engaged by said additional resilient means, said additional resilient means comprising an O-ring.

7. The combination as set forth in claim 1 wherein the first mentioned resilient means comprises a plastic disk.

8. The combination as set forth in claim 6 wherein the first mentioned resilient means comprises a plastic disk.

9. The combination as set forth in claim 1 wherein said housing is metallic.

10. The combination as set forth in claim 1 wherein a portion of said transducer extends from said housing and beyond the open end of said reflector.

11. The combination as set forth in claim 1 wherein the tapered end of the housing is dome-shaped, the balance of said housing being substantially cylindrical.

* * * * *